United States Patent
Gallovic et al.

(10) Patent No.: US 12,005,261 B2
(45) Date of Patent: Jun. 11, 2024

(54) PROGRAMMING OF PAIRING AND MRI MODES IN AN IMPLANTABLE MEDICAL DEVICE SYSTEM

(71) Applicant: Boston Scientific Neuromodulation Corporation, Valencia, CA (US)

(72) Inventors: Hannah Gallovic, Sherman Oaks, CA (US); Sridhar Kothandaraman, Valencia, CA (US); John Rivera, Oxnard, CA (US); Chirag Shah, Valencia, CA (US); Joshua Uyeda, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 266 days.

(21) Appl. No.: 17/447,381

(22) Filed: Sep. 10, 2021

(65) Prior Publication Data

US 2022/0096849 A1    Mar. 31, 2022

Related U.S. Application Data

(60) Provisional application No. 63/085,546, filed on Sep. 30, 2020.

(51) Int. Cl.
*A61N 1/372*    (2006.01)
*A61N 1/08*     (2006.01)

(52) U.S. Cl.
CPC ......... *A61N 1/37252* (2013.01); *A61N 1/086* (2017.08); *A61N 1/37217* (2013.01)

(58) Field of Classification Search
CPC .............. A61N 1/3718; A61N 1/37252; A61N 1/37217
See application file for complete search history.

(56) References Cited

U.S. PATENT DOCUMENTS

| | | |
|---|---|---|
| 6,516,227 B1 | 2/2003 | Meadows et al. |
| 7,242,981 B2 | 7/2007 | Ginggen |

(Continued)

FOREIGN PATENT DOCUMENTS

| | | |
|---|---|---|
| WO | 2011/100239 A1 | 8/2011 |
| WO | 2021/046120 | 3/2021 |

OTHER PUBLICATIONS

Boston Scientific Corp., "Vercise™ DBS Remote Control 4: Directions for Use" (2020; downloaded from Internet Sep. 14, 2020).

(Continued)

*Primary Examiner* — George R Evanisko
(74) *Attorney, Agent, or Firm* — Lewis & Reese, PLLC

(57) ABSTRACT

Systems and methods are disclosed for use with Implantable Medical Devices (IMD) such as Implantable Stimulator Devices. The system includes a permanent magnet which can be used to reset the IMD (such as during an emergency) and to place the IMD in a pairing mode to establish communications with an external device. An external device paired to the IMD can be used to place the IMD in an MRI mode that renders the IMD safe during a Magnetic Resonance Imaging (MRI) scan. In the event that the external device is unavailable to cause the IMD to exit the MRI mode, the bar magnet can also be used in the MRI mode to pair the IMD with another external device.

20 Claims, 6 Drawing Sheets

*MRI Mode with Pairing Mode:* t17:
- IPG in MRI mode
- Normal telemetry enabled with RC 50, BUT RC 50 not present (at t18).

t19:
- Sensor 40 detects bar magnet 90 t20:
- Bar magnet 90 removed from sensor 40
- If sensor 40 detected bar magnet 90 for 4s ≤ t ≤ 10s:
  • Enter pairing mode: IPG periodically broadcasts pairing data during transmission windows
  • IPG DOES NOT ENTER RESET MODE t21:
- RC 50' is present; Select IPG pairing at RC 50'; scan for IPGs
- RC 50' receives pairing data from IPG; user connects with IPG using RC 50' (IPG and RC50' are paired)
- IPG exits pairing mode, BUT IS STILL IN MRI MODE t22:
- Select exit MRI mode at RC 50'
- IPG receives exit MRI mode instruction at antenna 34a/b and exits MRI mode; enters normal mode
- Provide normal stimulation

(56) References Cited

U.S. PATENT DOCUMENTS

| | | | |
|---|---|---|---|
| 7,561,915 B1 * | 7/2009 | Cooke | A61B 5/055 |
| | | | 607/31 |
| 7,672,726 B2 | 3/2010 | Ginggen | |
| 7,996,079 B2 | 8/2011 | Armstrong | |
| 8,014,867 B2 | 9/2011 | Cooke et al. | |
| 8,090,445 B2 | 1/2012 | Ginggen | |
| 8,131,377 B2 | 3/2012 | Shi et al. | |
| 8,150,516 B2 | 4/2012 | Levine et al. | |
| 8,543,207 B2 | 9/2013 | Cooke et al. | |
| 8,838,254 B2 | 9/2014 | McClure et al. | |
| 8,983,615 B2 | 3/2015 | Tahmasian et al. | |
| 9,411,027 B2 | 8/2016 | Von Arx et al. | |
| 9,446,252 B2 | 9/2016 | Benson | |
| 9,463,322 B2 | 10/2016 | Wingeier et al. | |
| 9,707,402 B2 | 7/2017 | Aghassian | |
| 9,855,433 B2 | 1/2018 | Shahandeh et al. | |
| 9,867,983 B2 | 1/2018 | Doerr | |
| 9,894,691 B1 | 2/2018 | Hellman et al. | |
| 9,913,990 B2 | 3/2018 | Ter-Petrosyan et al. | |
| 10,286,209 B2 | 5/2019 | Yoon et al. | |
| 10,525,252 B2 | 1/2020 | Feldman et al. | |
| 10,589,090 B2 | 3/2020 | Feldman et al. | |
| 10,716,937 B2 | 7/2020 | Feldman et al. | |
| 2005/0070975 A1 | 3/2005 | Zeijlemaker et al. | |
| 2007/0173890 A1 | 7/2007 | Armstrong | |
| 2007/0191914 A1 | 8/2007 | Stessman | |
| 2008/0319497 A1 | 12/2008 | Griffith et al. | |
| 2011/0152972 A1 | 6/2011 | Doerr et al. | |
| 2012/0095529 A1 | 4/2012 | Parramon et al. | |
| 2015/0080982 A1 | 3/2015 | Funderburk | |
| 2015/0231402 A1 | 8/2015 | Aghassian | |
| 2015/0360038 A1 | 12/2015 | Zottola et al. | |
| 2016/0184591 A1 | 6/2016 | Feldman et al. | |
| 2018/0071513 A1 | 3/2018 | Weiss et al. | |
| 2018/0071520 A1 | 3/2018 | Weerakoon et al. | |
| 2018/0140831 A1 | 5/2018 | Feldman et al. | |
| 2019/0083802 A1 | 3/2019 | Legay et al. | |
| 2019/0344087 A1 | 11/2019 | Ter-Petrosyan et al. | |
| 2020/0001091 A1 | 1/2020 | Marnfeldt | |

OTHER PUBLICATIONS

Boston Scientific Corp., "Vercise™ Neural Navigator 4 Programming Manual: Directions for Use" (2020; downloaded from Internet Sep. 14, 2020).

Boston Scientific Corp., "ImageReady™ MRI Guidelines for Boston Scientific Deep Brain Stimulation Systems" (2020; downloaded from Internet Sep. 14, 2020).

Boston Scientific Corp., Vercise™ DBS Remote Control 4 Handbook (2020).

Cypress Semiconductor Corp., "PSoC Creator Component Datasheet: Bluetooth Low Energy (BLE) 1.20," p. 34 (2015).

Recommendation ITU-R RS 1346: Sharing Between the Meteorlogical Aids Service and Medical Implant Communication Systems (MICS) Operating in the Mobile Service in the Frequency Band 401-406 MHZ (1998).

Texas Instruments, Inc., data sheet for "CC2640R2F SimpleLink™ Bluetooth® 5.1 Low Energy Wireless MCU" (Jan. 2020).

International Search Report and Written Opinion regarding corresponding application No. PCT/US2021/071426, dated Jan. 4, 2022.

\* cited by examiner

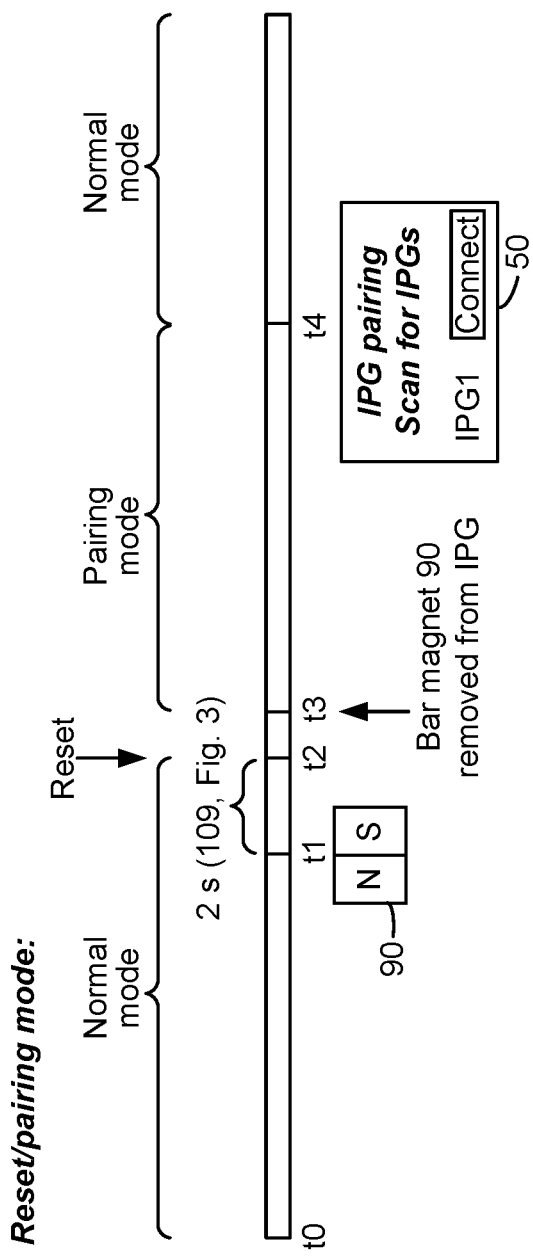

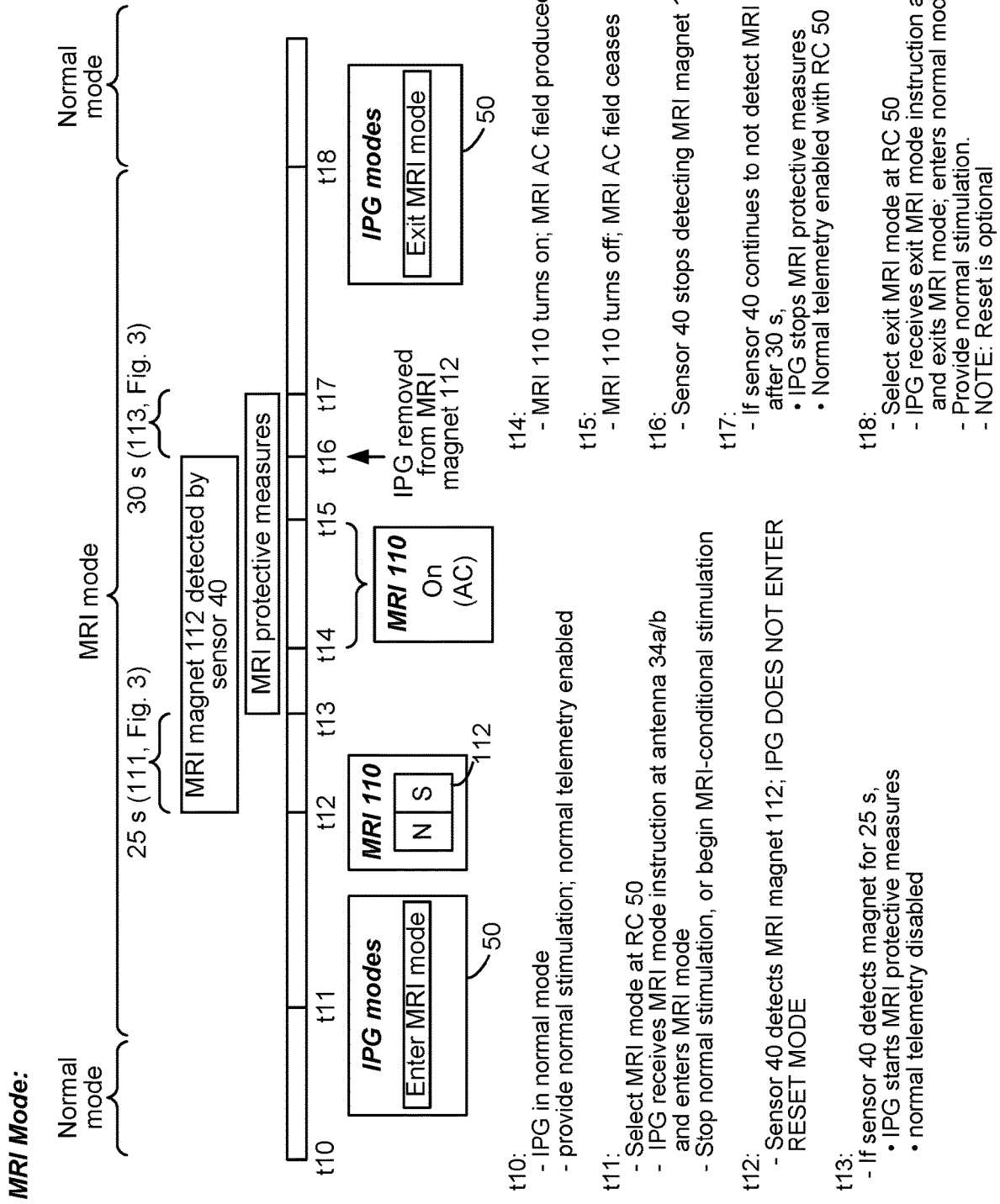

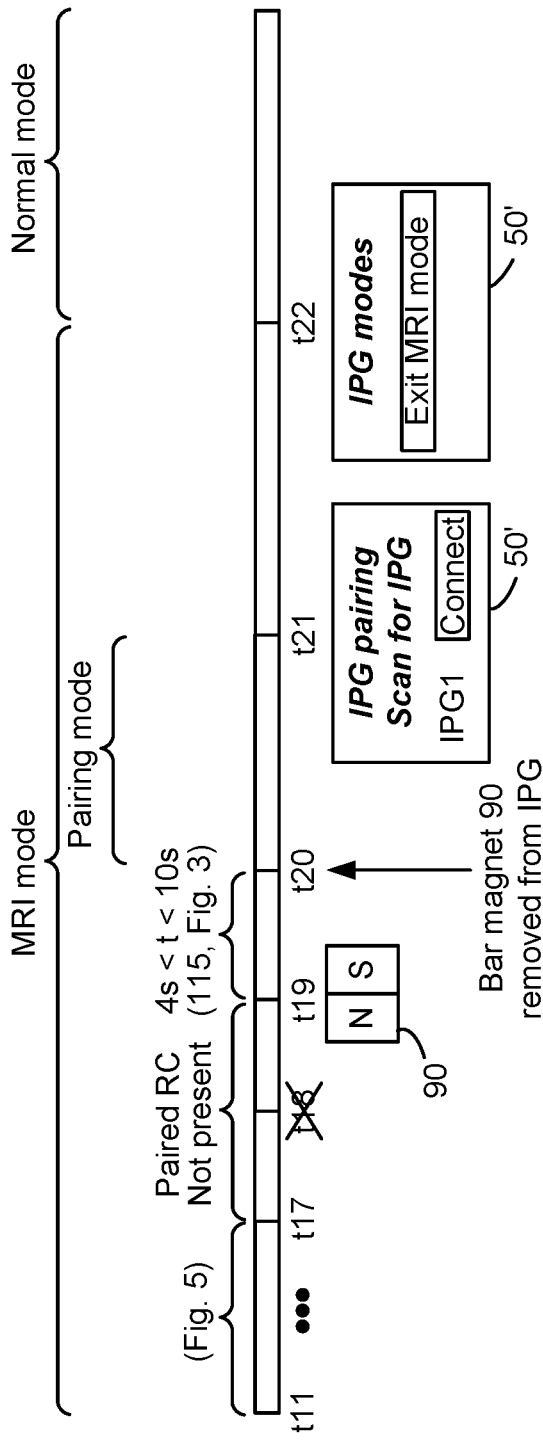

Figure 7

Mode logic 102

| IPG mode | Magnetic field sensed or not sensed at sensor 40 | (Assumed) magnetic field source | Action (Mode logic 102) |
|---|---|---|---|
| Normal mode | t ≥ 2s = A on (then off) | Bar magnet 90 | Reset, then pairing mode |
| MRI mode | t ≥ 25s = B on | MRI magnet 112 | Begin MRI protective measures; disable telemetry |
| MRI mode | t ≥ 30s = C off | MRI magnet 112 removed | Stop MRI protective measures; enable telemetry |
| MRI mode | 4s =D ≤ t ≤ 10s = E on (then off) | Bar magnet 90 | Pairing mode within MRI mode |

PROGRAMMING OF PAIRING AND MRI MODES IN AN IMPLANTABLE MEDICAL DEVICE SYSTEM

CROSS REFERENCE TO RELATED APPLICATIONS

This application is a non-provisional application of U.S. Provisional Patent Application Ser. No. 63/085,546, filed Sep. 30, 2020, to which priority is claimed, and which is incorporated by reference in its entirety.

FIELD OF THE INVENTION

This application deals with implantable medical device (IMDs) systems; the pairing of IMDs to external communication devices; and use of an MRI mode to render the IMD safe during an MRI scan.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Deep Brain Stimulation (DBS) or Spinal Cord Stimulation (SCS) system, such as that disclosed in U.S. Pat. No. 6,516,227 and U.S. Patent Application Publication 2016/0184591. However, the present invention may find applicability with any implantable neurostimulator device system.

A DBS or SCS system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array. For example, one or more percutaneous leads 18 can be used having electrodes 16 carried on a flexible body. In another example, a paddle lead 20 provides electrodes 16 positioned on one of its generally flat surfaces. Lead wires within the leads are coupled to the electrodes 16 and to proximal contacts 22 insertable into lead connectors 24 fixed in a header 26 on the IPG 10, which header can comprise an epoxy for example. Once inserted, the proximal contacts 22 connect to header contacts 28 within the lead connectors 24, which are in turn coupled by feedthrough pins 30 through a case feedthrough 32 to stimulation circuitry 36 within the case 12. The number and type of leads, and the number of electrodes on such leads, can vary depending on the application. The conductive case 12 can also comprise an electrode.

In a SCS application, as is useful to alleviate chronic back pain for example, the electrode lead(s) are typically implanted in the spinal column proximate to the dura in a patient's spinal cord, preferably spanning left and right of the patient's spinal column. The proximal contacts 22 are tunneled through the patient's tissue to a distant location such as the buttocks where the IPG case 12 is implanted, at which point they are coupled to the lead connectors 24. In a DBS application, as is useful in the treatment of tremor in Parkinson's disease for example, the IPG 10 is typically implanted under the patient's clavicle (collarbone). Percutaneous leads 18 are tunneled through and under the neck and the scalp where the electrodes 16 are implanted through holes drilled in the skull and positioned for example in the subthalamic nucleus (STN) and the pedunculopontine nucleus (PPN) in each brain hemisphere.

IPG 10 can include an antenna 34a allowing it to communicate bi-directionally with a number of external devices discussed subsequently. Antenna 34a as shown comprises a conductive coil within the case 12, although the coil antenna 34a can also appear in the header 26. When antenna 34a is configured as a coil, communication with external devices preferably occurs using near-field magnetic induction. IPG 10 may also include a Radio-Frequency (RF) antenna 34b. In FIG. 1, RF antenna 34b is shown within the header 26, but it may also be within the case 12. RF antenna 34b may comprise a patch, slot, or wire, and may operate as a monopole or dipole. RF antenna 34b preferably communicates using far-field electromagnetic waves, and may operate in accordance with any number of known RF communication standards, such as Bluetooth, Zigbee, WiFi, MICS, and the like. IPG 10 can also include functionally-similar devices that are not fully implantable in the patient. For example, the IPG 10 can comprise an External Trial Stimulator (ETS), having leads implantable in the patient but connected to a circuitry portion that is external to the patient. When an ETS is used, stimulation can be tried on a prospective implant patient without going so far as to implant the IPG's case 12. ETS devices are explained further in U.S. Patent Application Publication 2020/0001091.

Stimulation in IPG 10 is typically provided by pulses, as described in the above-referenced '091 Publication. Pulses can be formed by stimulation circuitry 36 in the IPG, again as described in the '091 Publication. Stimulation circuitry 36 can comprise a part of, or can communicate with, the IPG's control circuitry 38. The control circuitry 38 can comprise a microcontroller, microprocessor, Field Programmable Grid Array, Programmable Logic Device, Digital Signal Processor or like devices. In one example, control circuitry 38 can comprise or include an MSP430 microcontroller device, manufactured by Texas Instruments, Inc. Control circuitry 38 may also be based on well-known ARM microcontroller technology. Control circuitry 38 may include a central processing unit capable of executing instructions, with such instructions stored in volatile or non-volatile memory within the control circuitry. Control circuitry 38 may also include, operate in conjunction with, or be embedded within, an Application Specific Integrated Circuit (ASIC), such as described in U.S. Patent Application Publications 2008/0319497, 2012/0095529, 2018/0071513, or 2018/0071520, which are incorporated herein by reference. The control circuitry 38 may comprise an integrated circuit with a monocrystalline substrate, or may comprise any number of such integrated circuits. Control circuitry 38 may also be included as part of a System-on-Chip (SoC) or a System-on-Module (SoM) which may incorporate memory devices and other digital interfaces.

IPG 10 may also include a magnetic field sensor 40, such as a Hall effect sensor. Magnetic field sensor 40 can also comprise other devices or circuits in the IPG, for example as taught in U.S. Pat. No. 10,589,090 and U.S. Patent Application Publication 2007/0191914. Use of the magnetic field sensor 40 in an IPG 10 is explained further below.

FIG. 2 shows various external devices that can wirelessly communicate with the IPG 10, including a patient hand-held remote controller (RC) 50 and a clinician programmer (CP) 60. Both of devices 50 and 60 can be used to wirelessly transmit information, such as a stimulation program, to the IPG 10—that is, to program stimulation circuitry 36 to produce stimulation (e.g., pulses) with a desired amplitude and timing. Both devices 50 and 60 may also be used to adjust one or more stimulation parameters of a stimulation program that the IPG 10 is currently executing, to update software in these devices, or to place the IPG into different operational modes as discussed further below. Devices 50 and 60 may also wirelessly receive information from the IPG 10, such as various status information, etc.

Clinician programmer (CP) 60 is described further in U.S. Patent Application Publication 2015/0360038, and can comprise a computing device 62, such as a desktop, laptop, notebook computer, tablet, mobile smart phone, or Personal Data Assistant (PDA)-type mobile computing device, etc. In FIG. 2, computing device 62 is shown as a laptop computer that includes typical computer user interface means such as a screen 64, a mouse, a keyboard, speakers, a stylus, a printer, etc., not all of which are shown for convenience. Also shown in FIG. 2 are accessory devices for the CP 60 that are usually specific to its operation as a stimulation controller, such as a communication "wand" 66 coupleable to suitable ports on the computing device 62, such as USB ports 69 for example.

The antenna used in the CP 60 to communicate with the IPG 10 can depend on the type of antennas included in the IPG. If the patient's IPG 10 includes a coil antenna 34a, wand 66 can likewise include a coil antenna 70a to establish near-field magnetic-induction communications at small distances. In this instance, the wand 66 may be affixed in close proximity to the patient, such as by placing the wand in a belt or holster wearable by the patient and proximate to the patient's IPG 10. If the IPG 10 includes an RF antenna 34b, the wand 66, the computing device 62, or both, can likewise include an RF antenna 70b to establish communication at larger distances.

To program stimulation programs or parameters for the IPG 10, or to otherwise control the IPG 10, the clinician interfaces with a clinician programmer graphical user interface (GUI) 72 provided on the display 64 of the computing device 72. As one skilled in the art understands, the GUI 72 can be rendered by execution of clinician programmer software 74 stored in the computing device 72, which software may be stored in the device's non-volatile memory 76. Execution of the clinician programmer software 74 in the computing device 62 can be facilitated by control circuitry 78 such as one or more microprocessors, microcomputers, FPGAs, DSPs, other digital logic structures, etc., which are capable of executing programs in a computing device, and which may comprise their own memories. For example, control circuitry 78 can comprise an i5 processor manufactured by Intel Corp, as described at https://www.intel.com/content/www/us/en/products/processors/core/i5-processors.html. Such control circuitry 78, in addition to executing the clinician programmer software 74 and rendering the GUI 72, can also enable communications via antennas 70a or 70b to communicate stimulation parameters chosen through the GUI 82 to the patient's IPG 10.

Remote controller (RC) 50 can be as described in U.S. Patent Application Publication 2015/0080982 for example, and may comprise a controller dedicated to work with the IPG 10. RC 50 may also comprise a general purpose mobile electronics device such as a mobile phone which has been programmed with a Medical Device Application (MDA) allowing it to work as a wireless controller for the IPG 10, as described in U.S. Patent Application Publication 2015/0231402. Like the CP 60, RC 50 includes a graphical user interface including a display 52 and means for entering commands or selections, such as buttons 56 or selectable graphical elements rendered on the display. The RC 50's graphical user interface also enables a patient to adjust stimulation parameters, although it may have limited functionality when compared to the more-powerful CP 60 described above. The RC 50 can have one or more antennas capable of communicating with the IPG 10. For example, the RC 50 can have a near-field magnetic-induction coil antenna 54a capable of wirelessly communicating with the coil antenna 34a in the IPG 10. The RC 50 can also have a far-field RF antenna 54b capable of wirelessly communicating with the RF antenna 34b in the IPG 10. The RC 50 includes control circuitry 58 which may be similar to the control circuitry in the CP 60, and which includes memory for storing software and the like. The RC 50 typically has a battery (not shown) to provide operating power, and such battery is usually rechargeable (similar to a cell phone).

The IPG 10, RC 50, and CP 60, as well as communicating with each other, can communicate with a network 80. Network 80 can comprise a WiFi gateway and the Internet for example, and communication between the devices can occur using the network 80 as an intermediary. A server 81 can be connected to the network, which can for example be used to send stimulation programs or other useful information (e.g., software updates) to the various devices in the system.

FIG. 2 further shows a permanent bar magnet 90 in the communication system for the IPG 10. Use and function of the bar magnet 90 is described further below.

SUMMARY

A method is disclosed for controlling an implantable medical device (IMD), which may comprise: receiving at the IMD a first instruction to cause the IMD to enter a protective mode, wherein in the protective mode the IMD is enabled to execute one or more protective measures to protect the IMD from a first field produced by equipment; while in the protective mode, receiving at the IMD a second instruction to cause the IMD to enter a pairing mode, wherein the pairing mode enables the IMD to pair for communications with an external device; while in the protective mode and the pairing mode, receiving at the IMD, from a first external device, a third instruction to cause the IMD and the first external device to pair for communications; and while in the protective mode, receiving at the IMD, from the first external device, a fourth instruction to cause the IMD to exit the protective mode.

In one example, the first instruction is received at the IMD from a second external device paired for communications with the IMD, wherein the second external device is different from the first external device. In one example, the second instruction comprises a second magnetic field. In one example, the second magnetic field is produced by an external magnet. In one example, the second magnetic field comprises a DC magnetic field. In one example, the second magnetic field is effective to cause the IMD to enter the pairing mode when the second magnetic field is received at the IMD for a first duration. In one example, the first duration is between a minimum duration and a maximum duration. In one example, the IMD is programmed with the minimum duration and the maximum duration. In one example, the first field comprises an AC magnetic field produced by the equipment. In one example, the method further comprises, while in the protective mode, receiving at the IMD a fifth instruction from the equipment to cause the IMD to execute the one or more protective measures. In one example, the fifth instruction comprises a third magnetic field. In one example, the third magnetic field is produced by the equipment. In one example, the third magnetic field comprises a DC magnetic field produced by a magnet in the equipment. In one example, the third magnetic field is effective to cause the IMD to execute the one or more protective measures when the third magnetic field is received at the IMD for a second duration. In one example, the third magnetic field is effective to cause the IMD to stop executing the one or more protective measures when the third magnetic field is not received at the IMD for a third duration. In one example, the method further comprises periodically broadcasting pairing data from the IMD when the IMD is in the pairing mode. In one example, the protective mode comprises a Magnetic Resonance Imaging (MRI) mode, and wherein the equipment comprises an MRI machine.

A method for controlling an implantable medical device (IMD) is disclosed, which may comprise: receiving at the IMD a first instruction to cause the IMD to enter a protective mode, wherein in the protective mode the IMD is enabled to execute one or more protective measures to protect the IMD from a first field produced by equipment; while in the protective mode, detecting the presence of the equipment and thereafter executing the one or more protective measures; while in the protective mode, detecting the absence of the equipment and thereafter stopping the execution of the one or more protective measures; and receiving at the IMD a second instruction to cause the IMD to exit the protective mode.

In one example, the IMD is programmed with a first duration, wherein equipment is detected at a first time and wherein the one or more protective measures are executed the first duration after the first time. In one example, the IMD is programmed with a second duration, wherein the absence of the equipment is detected at a second time and wherein the one or more protective measures are stopped the second duration after the second time. In one example, the presence of the equipment is detected by detecting the first field produced by the equipment. In one example, the first field comprises an AC magnetic field. In one example, the presence of the equipment is detected by detecting a second magnetic field produced by the equipment. In one example, the second magnetic field comprises a DC magnetic field. In one example, the DC magnetic field is produced by a DC magnet in the equipment. In one example, the IMD comprises an implantable stimulation device configured to provide stimulation to a patient's tissue, and wherein entering the protective mode causes the stimulation to stop. In one example, exiting the protective mode causes the stimulation to begin. In one example, the IMD comprises an implantable stimulation device configured to provide normal stimulation or conditional stimulation to a patient's tissue, and wherein entering the protective mode causes the normal stimulation to stop and conditional stimulation to begin. In one example, exiting the protective mode causes the conditional stimulation to stop and the normal stimulation to begin. In one example, the IMD comprises an implantable stimulation device with stimulation circuitry configured to provide normal stimulation to a patient's tissue, wherein the one or more protective measures comprise one or more of the following: disabling the stimulation circuitry; starting conditional stimulation; increasing a power supply voltage of the stimulation circuitry; and/or opening switches in the stimulation circuitry. In one example, the method further comprises disabling telemetry at the IMD upon executing the one or more protective measures. In one example, the method further comprises enabling telemetry upon stopping the execution of the one or more protective measures. In one example, detecting the presence of the equipment does not comprise receiving wireless data telemetry from the equipment. In one example, exiting the protective mode causes the IMD to reset. In one example, the first and second instructions are received from one or more external devices. In one example, the protective mode comprises a Magnetic Resonance Imaging (MRI) mode, and wherein the equipment comprises an MRI machine.

A method for pairing an implantable medical device (IMD) for communications with an external device, wherein the IMD is configured to provide therapy to a patient. The method may comprise in order: (a) receiving at the IMD a DC magnetic field from an external magnet; (b) determining at the IMD whether the DC magnetic field is received for a duration, wherein the duration is programmed in memory in the IMD; (c) when the DC magnetic field is received for the duration, resetting the IMD, wherein the reset causes the IMD to stop providing the therapy; (d) if the DC magnetic field is received for longer than the duration, holding the IMD in reset; (e) determining at the IMD whether the DC magnetic field is no longer received at the IMD; and (f) when the DC magnetic field is no longer received, causing the IMD to enter a pairing mode, wherein the pairing mode enables the IMD to pair for communications with the external device.

In one example, the method further comprises in step (f), causing the IMD to start providing the therapy when the DC magnetic field is no longer received. In one example, the method further comprises, prior to step (a), operating the IMD in a normal mode, wherein in the normal mode the IMD provides the therapy. In one example, the method further comprising in step (f), periodically broadcasting pairing data from the IMD when the IMD is in the pairing mode. In one example, the external magnet comprises a permanent bar magnet. In one example, the method further comprising in step (e), exiting reset upon determining at the IMD that the DC magnetic field is no longer received at the IMD. In one example, the therapy comprises measurements taken by the IMD. In one example, the IMD comprises an implantable stimulation device (ISD), and wherein the therapy comprises stimulation provided to a tissue of a patient.

BRIEF DESCRIPTION OF THE DRAWINGS

FIG. 3 also shows mode logic operable in the IPG's control circuitry to place the IPG into different operating modes and to issue control signals operable with those modes.

FIG. 4 shows operation of a reset/pairing mode for the IPG, in which the IPG is responsive to the bar magnet to reset the IPG and to enter a pairing mode to enable the IPG to be paired with an external device.

FIG. 5 shows operation of an MRI mode for the IPG, which allows the patient to safely have an MRI scan.

FIG. 6 shows operation of a pairing mode operable within the MRI mode, which allows the IPG to be paired with a new external device that is not currently paired with the IPG.

FIG. 7 summarizes operation of the mode logic in the IPG, and in particular different actions that are taken by the IPG upon sensing magnetic fields in different modes.

DETAILED DESCRIPTION

A patient having an implanted IPG may from time to time need to undergo a medical procedure involving the use of high magnetic fields. For example, an IPG patient may require medical imaging using a Magnetic Resonance Imaging (MRI) machine 110 (FIG. 5). As is known, an MRI machine 110 includes a high-powered DC magnet 112 (FIG. 5) capable of producing a DC magnetic field with strengths of up to several Tesla. This DC magnetic field by itself is not usually harmful to the IPG 10, nor does it present a particular safety issue for the IPG patient. However, when an MRI machine is turned on, AC magnetic fields are produced, which can potentially harm the IPG 10 or the patient. Briefly, AC magnetic fields can induce currents in the IPG 10, and in particular in the IPG's leads, which can cause current to be injected into the IPG via the electrode connections. Such current injection can harm the IPG 10's circuitry, and can also produce uncontrolled stimulation in the patient's tissue.

Figure 1:
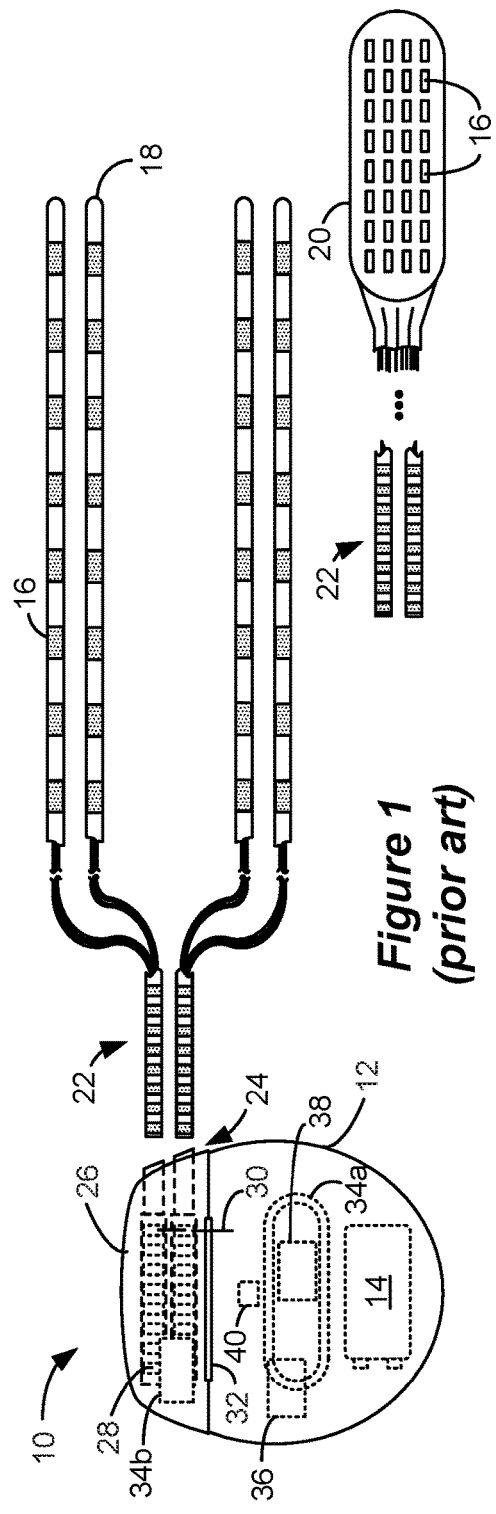
FIG. 1 shows an Implantable Pulse Generator (IPG), in accordance with the prior art.
Figure 2:
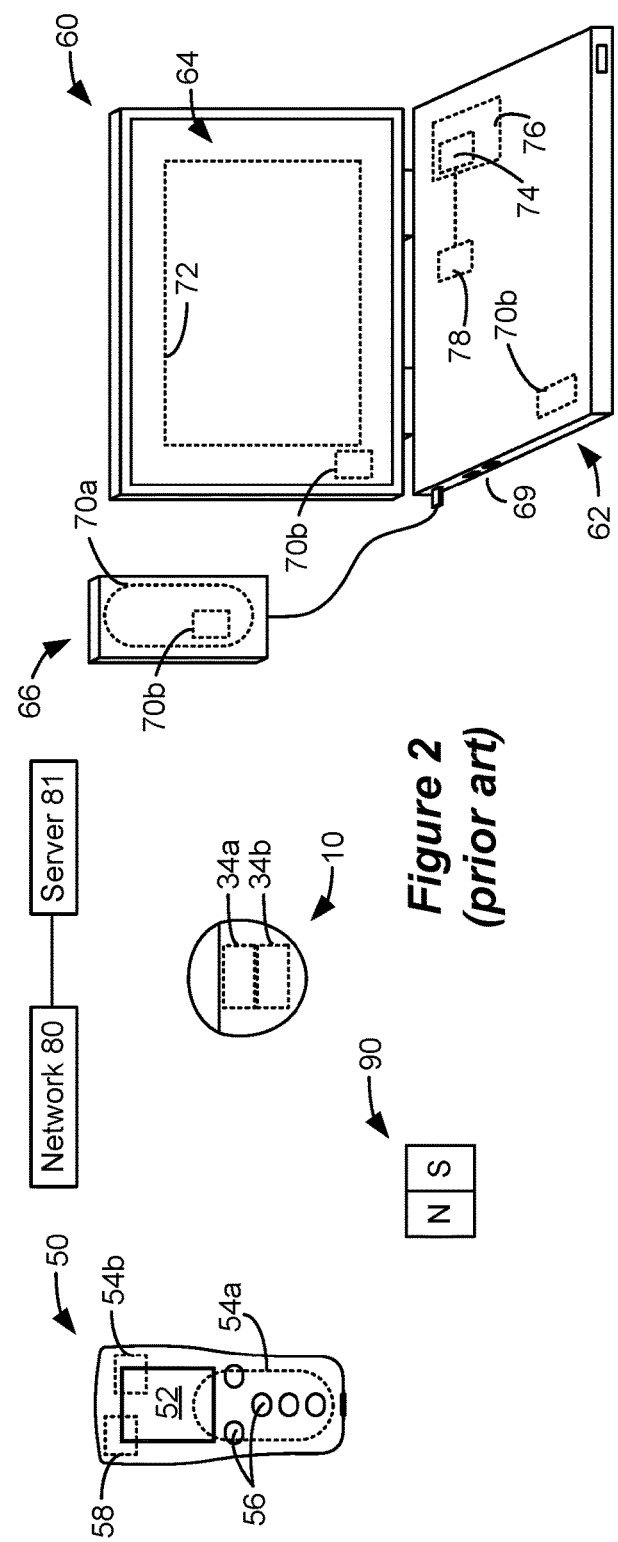
FIG. 2 shows various external devices capable of communicating with and programming stimulation in an IPG, in accordance with the prior art.

As a result, it is known to place an IPG 10 into an MRI mode prior to the patient receiving an MRI scan. As explained further below, the IPG can be placed wirelessly into an MRI mode using an external device, such as the patient remote controller 50 described earlier (FIG. 2). Even though a patient may have the ability to place his IPG 10 into MRI mode via his RC 50, often times a clinician will enter this mode on the patient's behalf in advance of the patient receiving an MRI scan, such as by using the patient's RC 50 or the clinician's CP 60.

When placed in the MRI mode, the IPG 10's control circuitry 38 can take one or more MRI protective measures to mitigate the potentially deleterious effects of the MRI scan. For example, in MRI mode, the control circuitry 38 may disable the stimulation circuitry 36 from providing stimulation to the patient, although this isn't always the case. In other examples, entering the MRI mode can allow the IPG 100 to provide MRI-conditional stimulation which may differ from normal stimulation otherwise provided when the IPG 100 is operating in a normal mode. Additionally or alternatively, when in the MRI mode, the control circuitry 38 may increase one or more voltages within the IPG 100 to prevent unwanted current induction into the IPG. For example, the control circuitry 38 may increase the power supply voltage for the stimulation circuitry 36—typically known as the compliance voltage—to a maximum value (e.g., 18V). See, e.g., U.S. Pat. No. 10,525,252 and PCT (Int'l) Patent Application Publication WO 2021/046120, which are incorporated herein by reference (discussing the compliance voltage and its adjustment in an IPG). The IPG may also modify or suspend other operations in MRI mode. For example, the control circuitry 38 may open passive charge recovery switches in the stimulation circuitry 36. These switches are connected to the electrodes, and when closed will passively couple charge to an AC ground. See, e.g., U.S. Pat. No. 10,716,937 and U.S. Patent Application Publication 2018/0140831, which are incorporated herein by reference (discussing passive charge recovery switches). Because these switches can potentially create a path for MRI-injected electrode currents, they are opened during MRI mode.

After the patient has received their MRI scan, the IPG 10 preferably exits the MRI mode and assumes operation in a normal mode, including the provision of normal stimulation. Normally, the MRI mode can be exited as it was entered—though use of the patient's RC 50 or another external device with which the IPG is paired. However, experience teaches that not all patients will have their RCs 50 readily available after their MRI scan, and thus are at risk of being unable to exit the MRI mode. This could occur for any number of reasons. A patient may not be accustomed to using their RC, may not often carry it, may not keep it charged, or their RC may simply be broken. If the patient's IPG 10 was placed into MRI mode by the clinician, the chances increase that the patient will be reliant on the clinician to control such modes, meaning that the patient will likely not have their RC 50 at the end of the MRI scan, and instead will need to rely on the clinician to exit this mode. A patient may also need an MRI scan on an emergency basis, and may not have access to their RC 50 at the time of the scan. Regardless of the reason for the patient not having their RC 50, the inability to exit MRI mode can be a substantial problem. As noted above, normal stimulation is usually suspended upon entering the MRI mode, and if a patient cannot exit such mode, they will be unable to receive such therapy. Even if MRI-conditional stimulation is provided to the patient while the IPG 100 is in the MRI mode, such stimulation may not be optimal when compared to normal stimulation.

The above problems can be addressed by programming an IPG 100 appropriately, and by modifying the manner in which the IPG 100 operates in different modes. In accordance with the disclosed techniques, another external device, and in particular another RC 50' which may not have been previously paired to the IPG 100, can be used to take the IPG 100 out of MRI mode, and to resume operation in a normal mode.

Figure 3:
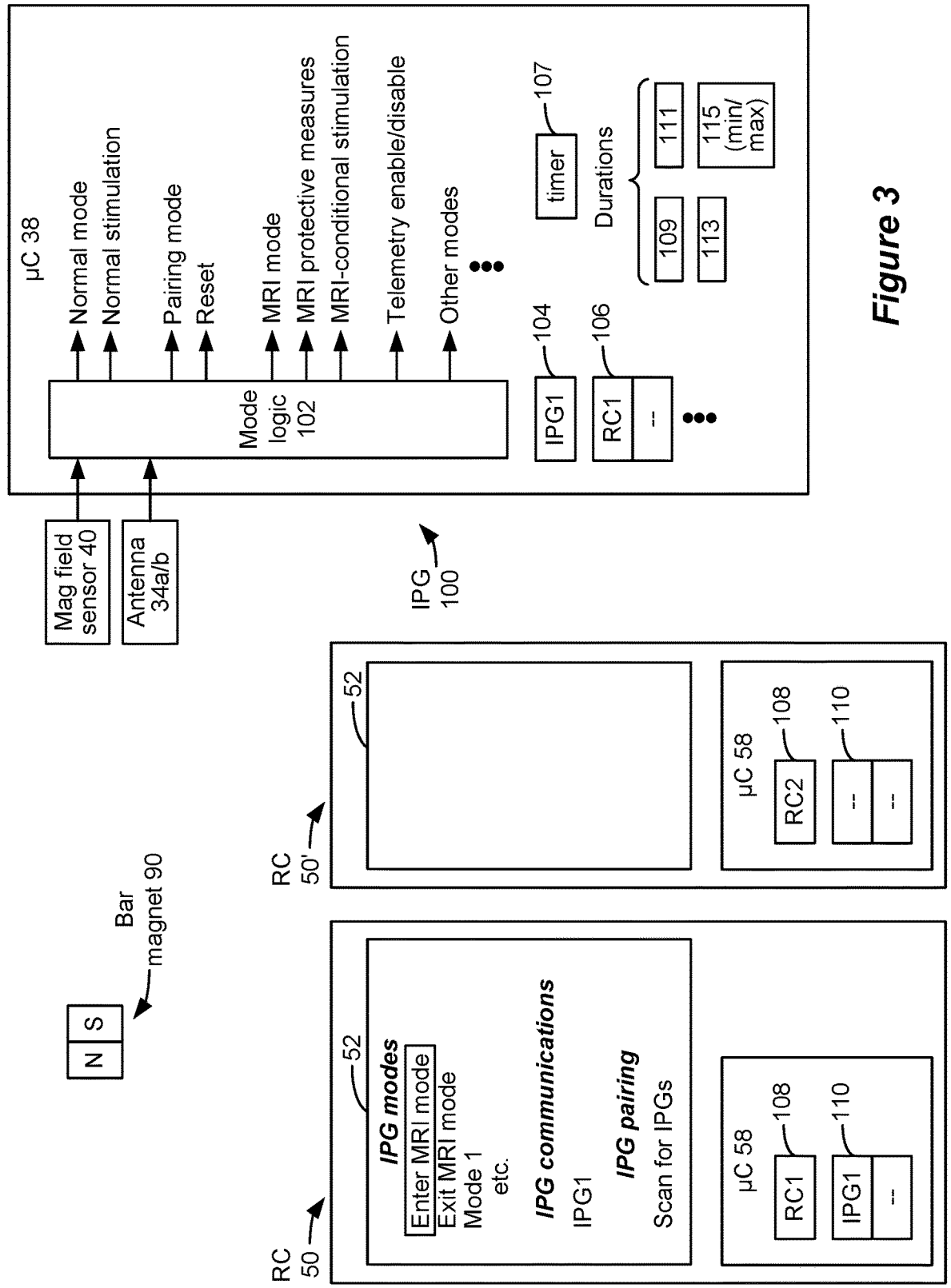
FIG. 3 shows a communication environment useable with the IPG in accordance with aspects of the invention, including a patient remote controller paired to the IPG, another external device which is not paired to the IPG, and bar magnet.

FIG. 3 shows a communication environment of an improved IPG 100, including various external devices that can be implicated in the practice of the disclosed techniques. Such external devices include the patient RC 50. The RC 50's control circuitry 58 can include or communicate with memory 108 that stores an ID code (RC1) for the RC 50. This ID code may be stored with other credentials or certificates that allow the RC 50 to communicate with various IPGs such as IPG 100. The RC's control circuitry 58 can also include a memory 110 that stores the ID codes (and other credentials and certificates) for IPGs with which the RC 50 has previously been paired for communications. In this example, it is assumed that RC 50 has previously been paired with IPG 100, and thus stores that IPG's ID code (IPG1). Notice that the IPG's control circuitry 38 can have similar memories 104 and 106 that respectively store the IPG's ID code (IPG1), and the ID code of previous RCs with which it has been paired (such as RC1). Again, the ID codes stored in memories 104 and 106 may be stored with other credentials or certificates as necessary to communicate with external devices such as RC 50. RC 50's GUI can include an option that allows the user to review IPGs to which it is currently paired ("IPG communications"), which can populate information stored in memory 110. RC's GUI can further include an option to allow RC 50 to be paired with a new IPG ("IPG pairing"), which when selected can cause the RC 50 to scan for new IPGs, as explained further below.

In the example shown, an "IPG modes" portion of the RC 50's GUI can allow the patient (or clinician) to cause the IPG 100 to enter different operational modes. For example, the RC 50 can include a selectable option to enter the IPG 100 into the MRI mode described previously, or to exit that mode, as explained further below. A user may also use the RC 50 to select other IPG 100 operational modes (Mode 1, Mode 2, etc.), although such other modes are not relevant to the present disclosure. In some examples, the RC can include a selectable option to allow the IPG 100 to operate in its normal mode, although mode logic 102 in the IPG 100 may also cause the IPG to operate in the normal mode automatically, as explained further below.

Relevant external devices in the system can include another RC 50' which has not been previously paired to the IPG 100. RC 50' stores its ID code (RC2) in its memory 108, but notice that its memory 110 is blank because this RC 50' has not been previously paired with another IPG (or at least in this example has not been previously paired with IPG 100). As explained further below, RC 50' can be used to cause the IPG 100 to exit MRI mode (after an MRI scan), which is especially useful if the patient does not have access to RC 50 already paired to the IPG 100. In this example, it is assumed for simplicity that RC 50' comprises a remote controller similar or identical to remote controller 50. However, RC 50' could comprise any new device in the communication system, such as the clinician programmer 60, or another external device capable of communicating with the IPG 100.

Also relevant in the communication environment of FIG. 3 is bar magnet 90. Bar magnet 90 is provided to the patient upon implantation of IPG 100, and can be used by the patient to cause a "reset" of the IPG 100. For example, if the patient is experiencing severe side effects or problems related to the stimulation therapy that the IPG 100 is providing, the patient can place the bar magnet 90 proximate to the IPG 100 to cause it to enter a reset mode. In the reset mode, the IPG 100's control circuitry 38 can suspend the delivery of stimulation to the patient, as discussed further below. Reset can also suspend telemetry and otherwise operate the IPG 100 in a low power state. Bar magnet 90 can also have other functions in the system, and in particular can be used to pair RCs with the IPG 100, again as discussed further below.

FIG. 3 also shows the basic circuitry in the IPG 100 that is implicated by the disclosed techniques. IPG 100 includes the control circuitry 38 mentioned earlier, although when used with the disclosed techniques this control circuitry 38 is programmed in a unique manner. In particular, mode logic 102 within the control circuitry 38 is programmed to place the IPG 100 into different modes and under certain conditions as explained further below. Such modes include a normal mode, which comprises the basic mode in which the IPG 100 is active and providing normal stimulation to the patient; the MRI mode discussed above (which may cause normal stimulation to cease, or which can be used to provide MRI-conditional stimulation); and a pairing mode used for pairing the IPG 100 for communications with an external device. The mode logic 102 can also issue certain control signals which may be associated with one of more of these modes. For example, when in the normal mode, a normal stimulation control signal indicates whether normal stimulation can commence. An IPG reset control signal, as well as resetting the IPG, can cause the IPG to operate in the pairing mode, although this depends on whether or not the IPG is currently in the MRI mode, as explained further below. An MRI protective measure control signal can indicate when certain MRI protective measures such as those mentioned above should be executed, and as explained further below, this control signal is issued at certain times during the MRI mode. An MRI-conditional stimulation control signal indicates when MRI-conditional stimulation can issue when the IPG is in the MRI mode. A telemetry enable/disable control signal can be used to enable or disable the IPG 100 to communicate with external devices to which it is paired. Mode logic 102 may also place the IPG 100 into other various modes, but those modes are not relevant to discuss here.

The mode logic 102 is responsive, at least, to the magnetic field sensor 40 in the IPG 100, and to commands that are received at the IPG's antenna 34a and/or 34b. Magnetic fields received by the magnetic field sensor 40 and commands received at the IPG's antenna may be generally considered as "instructions," because either can inform the mode logic 102 how to operate. Although not shown, one skilled will understand that the IPG 100 would include demodulation circuitry to convert telemetry received at the antenna 34a/b into digital information understandable by the mode logic 102. As noted earlier and as relevant to external communications, IPG 100's control circuitry 38 can include or communicate with memory 104 that stores an ID code (IPG1) for the IPG 100, and memory 106 that stores ID codes for previously-paired RCs, as well as other necessary credentials or certificates.

Also included in the control circuitry 38 is timer circuitry 107. The timer 107 is useful to determine whether certain durations have run. Such durations are programmable in memory, and include a normal pairing duration (109), a detect field onset duration (111), a detect field offset duration (113), and a MRI pairing duration (115), which can have minimum and maximum values. These durations are described further below.

FIGS. 4-6 discuss different IPG modes, how such modes and entered and exited, and how such modes function in the IPG 100. FIG. 4 shows a reset/pairing mode, which, as controlled by mode logic 102, combines the processes of placing the IPG 100 into reset followed by placing the IPG in a pairing mode that allows the IPG to establish communications with an external device. In FIG. 4, the reset/paring mode shows operation to pair the IPG with an RC 50, although pairing with another external device, such as the CP 60, would occur similarly.

The reset/pairing mode is discussed chronologically, and at t0 it is assumed that the IPG 100 is operating in a normal mode. In the normal mode, the IPG 100 is controlled (by mode logic 102) to provide normal stimulation. Normal telemetry is also enabled in the normal mode, as are other IPG functions not relevant to mention here. When normal telemetry is enabled, the IPG 100 can freely communicate with external devices, such as RC 50, with which the IPG 100 has already been paired, exchanging previously stored credentials or certificates as necessary. Preferably, to save power in the IPG 100, normal telemetry is enabled by periodically powering the antennas 34a or 34b in the IPG 100 and any associated communication circuitry (e.g., modulation and demodulation circuitry) during short listening windows (e.g., 10 ms) which are issued and at a period of about 1-3 seconds. How normal telemetry occurs with a paired RC can depend on the type of connection to be established and the communication standard that governs that connection. For example, if Bluetooth or Bluetooth Low Energy (BLE) is used for the connection, the IPG 100 can listen for a broadcast from RC 50 during each of the listening windows. Upon receiving proper credentials from RC 50 (such as the RC's ID code RC1, stored in the IPG's memory 106), a communication session can be established, at which time the IPG 100 can continuously power its antenna 34a or 34b and associated communication circuitry until the end of the communication session. Communication sessions can also be governed by communication intervals that also involve periodic powering of the telemetry circuitry. For example, when BLE communications are used, the connection interval can be in the range of 15 to 45 ms.

At time t1, bar magnet 90 is placed over (or proximate to) the IPG 100. The magnetic field sensor 40 in the IPG 100 detects the magnetic field produced by the bar magnet 90, and provides information to the mode logic 102 that a magnetic field is present. The mode logic 102 monitors the output of the sensor 40 to determine whether a magnetic field is consistently detected for a time period, such as 2 seconds or more. This time period, called the normal pairing duration, can be programmed in memory 109 (FIG. 3), and can be monitored by the timer 107 (FIG. 3). Requiring the presence of a continuous magnetic field for a time period is preferred to ensure that the IPG 100 isn't inadvertently placed into the reset/pairing mode by a transient magnetic field to which the patient might be exposed.

If the bar magnet 90 is present for the time period, the mode logic 102 issues a reset at time t2. Different functions in the IPG 100 can be affected upon reset, but significantly here the reset disables the stimulation circuitry 36 and thus normal stimulation is stopped. In this respect, the bar magnet 90 acts as a safety device by providing the patient a means for stopping stimulation on an emergency basis. For example, if the stimulation being provided by the IPG 100 is proving problematic for the patient, and the patient is not able to quickly remedy the situation using their RC 50, the bar magnet 50 provides a quick and safe means of easily stopping stimulation. In this regard, note that if the magnetic field is present and detected by the magnetic field sensor 40 for longer than the two-second time period, the mode logic 102 will hold the IPG in reset (from t2 to t3) until the bar magnet 90 is removed. Therefore, a patient experiencing problems can simply keep the bar magnet 90 continually proximate to the IPG to keep it in reset, and to prevent potentially problematic stimulation from re-occurring. (In this circumstance, the IPG patient would normally promptly make an appointment to see his clinician to attempt to rectify the problem). Use of a bar magnet 90 to cause a reset, and the actions that can occur in the IPG 100 when such a reset is issued, are discussed further in U.S. Pat. No. 8,473,070.

At time t3, the bar magnet 90 is removed from the IPG, and thus sensor 40 stops detecting its magnetic field. The mode logic 102 then, once the reset procedure is completed (which may take a few seconds) causes the IPG 100 to exit reset. Upon exiting reset, the mode logic 102 again enables normal stimulation, and as is most significant here also preferably automatically causes the IPG to enter the pairing mode. Other conditions not mentioned here may also need to occur before automatically entering the pairing mode.

In the pairing mode, the IPG 100 attempts to pair with an external device. During the pairing mode, the IPG 100 will periodically broadcast pairing (advertising) data. To save power, such pairing data may be periodically broadcast during transmission windows, such as every 0.5 seconds. In one example, the pairing data can comprise the IPG's ID code or serial number ("IPG1," memory 104), which the RC 50 may recognize (if stored in memory 110). The pairing data can also comprise additional data necessary for authentication, which may be necessary to allow the IPG 100 to be paired with a previously-unknown external device. In this regard, the pairing data may depend on the type of connection to be established and the communication standard that govern that connection. For example, if Bluetooth or BLE is used, that standard will dictate the particulars of the pairing data to be broadcast by the IPG 100. During pairing mode, the IPG 100 can still receive communications from external devices that were previously paired to the IPG, and should this occur, the pairing mode is exited at the IPG.

At time t4, it is assumed that an external device, such as RC 50, is present (i.e., proximate to the IPG 100) and able to pair with the IPG 100. The user selects the IPG pairing mode at the GUI of the external device (e.g., RC 50) to scan for available IPGs, and selects the option to connect with IPG 100. At this point, RC 50 receives the pairing data being broadcast from IPG 100. If the pairing data includes IPG data already known to the RC 50, such as the IPG 100's ID code (IPG1) stored in RC 50's memory 110, pairing and connection with IPG 100 can be simplified. For example, if RC 50 and IPG 100 were previously paired (as is assumed here), each device would know that fact, as each has stored the other's ID codes and other certificates and credentials (see memories 106 and 110, FIG. 3). If the pairing data does not include IPG data already known to the RC 50, additional authentication data may be required to allow the devices to pair. For example, the user may need to enter a password or PIN for the IPG 100 in the GUI of the RC 50, or authentication can occur automatically through the exchange of secure keys at part of an authentication procedure. Again, the particulars of the pairing data and the data exchanged to allow the RC 50 to connect to a new IPG 100 may differ depending on the communication standard used, which can vary in different implementations.

It is preferred that the IPG not operate in the pairing mode indefinitely. In this regard, a pairing mode duration may be set and stored with the IPG's control circuitry 38 and/or mode logic 102. This pairing mode duration is preferably long enough to give the user of the external device (e.g., RC 50) time to complete the pairing procedure using the RC's GUI as just explained. In one example, the pairing mode duration may be about 2 minutes. After expiration of the pairing mode duration, the mode logic 102 preferably cusses the IPG to revert to operation in its normal mode. Details concerning this pairing mode duration are omitted from the Figures for simplicity.

Once the IPG 100 and RC 50 are paired and connected at time t4, the mode logic 102 in the IPG's control circuitry 38 can cause the IPG exit the pairing mode, and to automatically enter the normal mode. Normal stimulation started at t3 thus can continue, and normal telemetry can be enabled with the now-paired RC 50. Although not shown, both the IPG and the external device (e.g., RC 50), can store information relevant to the device with which its now paired, e.g., by storing relevant information about the other device in memories 106 and 110 (FIG. 3), and this may be especially useful to do if this is the first time that the IPG and external device are being paired.

FIG. 5 shows the MRI mode. At time t10, the IPG 100 is operating in the normal mode, and is providing normal stimulation. Normal telemetry is also enabled with RC 50, to which the IPG 100 is currently paired. At time t11, the IPG 100 is placed in MRI mode, which occurs using the GUI of paired RC 50, as explained earlier. This causes RC 50 to transmit an MRI mode instruction to the IPG 100, which is received at the IPG's antenna 34a or 34b. At this point, normal stimulation is stopped. Additionally, if the IPG 100 is capable of providing MRI-conditional stimulation as described earlier, such conditional stimulation can be commenced. As noted earlier, MRI mode is entered in advance of the patient receiving an MRI scan. The delay between entering the MRI mode (t11) and the beginning of the MRI scan (t12) can comprise anywhere between a few minutes or a number of days.

At time t12, it is assumed that the patient is proximate to the MRI machine 110 and is getting ready to have their MRI scan taken. At this point, the magnetic field sensor 40 in the IPG 100 will detect the presence of the large DC magnet 112 in the MRI machine. As such, the IPG 100 detects the MRI machine 110 without receiving wireless data from the medical equipment. Note in this example that the magnetic field sensor 40 is unable to differentiate between a magnetic field produced by the bar magnet 90 (FIG. 4) and the magnetic field produced by the MRI magnet 112. This is however not problematic, because the mode logic 102 in the IPG 100 will assess the duration of such fields, and make informed determinations as necessary to operate the IPG in a proper mode, as explained further below.

The mode logic 102 will also enter modes conditionally depending on the IPG's current operating mode. For example, at time t12, the mode logic 102 will not issue a reset when the IPG 100 is in the MRI mode, even if the magnetic field (from magnet 112) is present for more than 2 seconds. Compare FIG. 4, where the mode logic 102 issues a reset when the IPG 100 is in a normal mode. When a magnet is sensed in MRI mode, it is preferred to not issue a reset (compare t2, FIG. 4), as this could hamper the IPG 100's ability to provide MRI protective measures, as described next. Note that the magnetic field sensor 40 will detect the MRI magnet 112 at time t12 when the patient is merely proximate to the MRI machine 110, such as when the patient is in the room containing the MRI machine 110, or is laying in the MRI's machine's bed. In short, the MRI machine may not yet be operating when the MRI magnet 112 is detected at time t12.

When the IPG 100 is in the MRI mode, the mode logic 102 will assess whether any magnetic field (presumably, but not necessarily, from the MRI magnet 112) is sensed by magnetic field sensor 40 for a time period, such as 25 (X) seconds. This time period, called the detect field onset duration, can be programmed in memory 111 (FIG. 3), and can be monitored by the timer 107 (FIG. 3). This time period is preferably long for a couple of reasons: first, to ensure that the MRI magnet 112 is continuously detected (as opposed to transient magnetic fields); second, to differentiate detection of the MRI from the bar magnet 90 which can also be used during MRI mode, as explained further below with reference to FIG. 6.

If the magnetic field sensor 40 detects a magnetic field for this time period, at time t13, the IPG 100 automatically starts executing MRI protective measures. These MRI protective measures were discussed previously, and can include: disabling normal stimulation, or providing MRI-conditional stimulation (although this may also preferably have occurred earlier at time t11); increasing voltages within the IPG 100, such as the compliance voltage; opening passive charge recovery switches; etc. As noted earlier, because some of these MRI protective measures involve use of the IPG's stimulation circuitry 36, it is preferred that no reset issues in the MRI mode (between t12 and t13) as this may disable the stimulation circuitry.

Note that the MRI protective measures are preferably automatically executed by mode logic 102 at t13 (after 25 s) even is the MRI machine 110 is not yet on and producing an AC magnetic field. As noted earlier, it is these AC magnetic fields that are of potential concern, as they can cause AC current injection into the IPG 100. In this regard, note that the time period between the detection of the MRI's DC magnetic 112 (t12), and the start of AC magnetic fields by the MRI machine (at t14) would normally be significantly longer than 25 seconds, because it will normally take longer than this to get the patient situated in the MRI machine 110 before the MRI machine is turned on. As such, the MRI protective measures are executed in the IPG 100 in advance of the potentially-harmful AC magnetic fields. At time t13, normal telemetry is also preferably disabled, although this could also have occurred earlier in the MRI mode. Disabling normal telemetry causes the IPG 100 to stop issuing listening windows, which prevents the IPG 100 from communicating with its current-paired RC 50.

At time t14, it is assumed that the MRI machine 110 is now operating and is producing an AC magnetic field, although as just noted the IPG 100 has likely already began executing MRI protective measures at time t13. At time t15, the AC magnetic fields have ceased and the MRI machine 110 is still off, and thus the patient's MRI scan is complete. (Note that the IPG's magnetic field sensor 40 does not in this example sense the presence or termination of the AC magnetic fields, although that is possible in other embodiments). Even after the MRI machine 110 is turned off at time t15, the patient is still proximate the MRI machine 110, and so the magnetic field sensor 40 continues to sense the MRI machine's DC magnet 112.

At time t16, it is assumed that the patient is no longer proximate to the MRI machine 110, and therefore that magnetic field sensor 40 is no longer sensing the presence of the MRI machine's magnet 112. At this point, mode logic 102 assesses whether magnetic fields have consistently ceased for a time period, such as 30 (Y) seconds. This time period, called the detect field offset duration, can be programmed in memory 113 (FIG. 3), and can be monitored by the timer 107 (FIG. 3). If so, at time t17, MRI protective measures are stopped, and normal telemetry is once again enabled. Preferably, the duration that the DC magnetic field is detected (X=25 s) to enter the MRI protective measures (at t13) is different from the duration that the DC magnetic field is not detected (Y=30 s) when determining when to stop the MRI protective measures (at t17).

Even though the IPG 100 and mode logic 102 can be fairly confident at this point that the patient's MRI needs are over, the IPG 100 is still operating in the MRI mode, and it is preferred to affirmatively exit this mode once it is clear that MRI intervention is no longer a concern. Because normal telemetry is now enabled (t17), the MRI mode can be exited using the RC 50 with which the IPG 100 is paired, and this occurs at time t18. As shown, the patient (or clinician) can select the MRI modes menu in the GUI, and can select to exit the MRI mode. This causes RC 50 to transmit an exit MRI mode instruction to the IPG 100, which is received at the IPG's antenna 34a or 34b. At this point, mode logic 102 can cause the IPG 100 to enter the normal mode, which can automatically cause normal stimulation to begin (and cause any MRI-condition stimulation to stop).

Although not shown in FIG. 5, exiting the MRI mode at time t18 can also include resetting the IPG. In this example, when the IPG receives the exit mode instruction at t18, the mode logic 102 issues a reset. As explained earlier, this causes stimulation to stop (momentarily), and the pairing mode to begin (when stimulation commences again). Even though the user had just used the RC 50's GUI to send the exit MRI mode instruction, the user will thus have to use the RC 50's GUI again re-pair with the IPG so that the pairing mode can be exited, and the normal mode entered, as described earlier. While incorporating a reset with exiting the MRI mode is not strictly required, this can be sensible to ensure that the IPG returns to a normal state after experiencing the MRI environment.

As noted earlier, a potential problem with operation as described thus far can occur if the patient does not have his RC 50 at time t18 and so is unable to exit the MRI mode. In this circumstance it may be necessary to use a new external device that is not paired with the IPG 100. The mode logic 102 is thus programmed to allow the IPG 100 to be paired to a new external device while in the MRI mode, as shown in FIG. 6. In FIG. 6, it is assumed that this new external device comprises RC 50', although again another type of external device could be used as well.

As was the case earlier (FIG. 4), bar magnet 90 can be used as the means for pairing in the pairing mode. However, as FIG. 6 explains, modifications to the programming are made to allow the mode logic 102 to differentiate magnetic fields detected by the magnetic field sensor 40 when in the MRI mode. Such differentiation occurs through sensing the length of time that such magnetic fields are detected by the magnetic field sensor 40. As noted earlier with respect to FIG. 5, detection of a magnetic field for 25 s or more signals the mode logic to being executing MRI protective measures (t13, FIG. 5), the assumption being that the magnetic field in this circumstance must be caused by the MRI magnet 112. By contrast, detection of a magnetic field for a significantly shorter duration will signal the mode logic 102 to enter the pairing mode (t20, FIG. 6), the assumption being that the magnetic field in this circumstance is caused by the bar magnet 90. Distinguishing the magnetic fields in this manner is important to allowing the mode logic 102 to take appropriate steps when magnetic fields are detected in the MRI mode. The pairing mode preferably comprises a sub-mode with the MRI mode, as shown in FIG. 6.

FIG. 6 starts with t17 (FIG. 5), with the IPG 100 in the MRI mode. It is assumed here that that t17 occurs after the patient's MRI scan and after MRI protective measures have ceased. However, it may also be the case at time t17 that the patient's MRI scan never occurred (e.g., it was canceled). In short, the IPG 100 may have been placed in the MRI mode (t11, FIG. 5), but steps shown at times t12-16 (FIG. 5) never occurred.

In any event, at time t17 in FIG. 6 and during the MRI mode, normal telemetry is enabled and thus IPG 100 is able to communicate with RC 50 to which it is currently paired. However, RC 50 is not present in this example (as occurred at t18 in FIG. 5), and instead the IPG 100 will be paired with a new RC 50'. As noted above, such pairing occurs using bar magnet 90, which at time t19 is brought proximate to the IPG 100 to commence the pairing mode. At t19, the bar magnet 90 starts to be sensed by the IPG's magnetic field sensor 40, and mode logic 102 determines the duration that this magnetic field is present. As noted above, when in the MRI mode, the mode logic will take certain actions—such as initiating MRI protective measures, t13, FIG. 5—if the magnetic field is detected for a relatively long time (≥25 s). It is not desired in FIG. 6 that such MRI protective measures are (again) executed at time t19. To ensure this, the user is instructed to hold the bar magnet 90 proximate to the IPG 100 for a time period between 4 and 10 seconds, and then to remove the bar magnet. Notice that this time period is easy for the user to estimate; its minimum value is suitably long to differentiate from transient fields; and its maximum value is significantly shorter than the duration necessary to start MRI protective measures (e.g., 25 s). In short, by controlling the time period during which the bar magnet 90 is proximate to the IPG 100, the user can cause the mode logic 102 to enter the pairing mode without taking other actions such as executing MRI protective measures.

At time t20, the bar magnet 90 is removed and no longer sensed. If the mode logic 102 determines that the magnetic field was present for the specified time period (4 s≤t≤10 s), the pairing mode is entered. This time period, called the MRI pairing duration, can be programmed in memory 115 (FIG. 3), including both its minimum (e.g., 4s) and maximum (e.g., 10s) values. Like other durations programmed in the IPG, this duration can be monitored by the timer 107 (FIG. 3). Thus, the IPG 100 can periodically broadcast pairing data during transmission windows. Note when entering the pairing mode from the MRI mode, the mode logic 102 will preferably not issue a reset. (Compare, FIG. 4, when in normal mode, a reset precedes entry into the pairing mode). As noted earlier, a reset would stop stimulation and telemetry as well, and is unnecessary in the context of FIG. 6.

At time t21, it is assumed that new RC 50' is present (i.e., proximate to the IPG 100) and able to pair with the IPG 100. The user selects the IPG pairing mode at the GUI of RC 50' to scan for available IPGs. At this point, RC 50' receives the pairing data being broadcast from IPG 100, and the user can then select the option to connect with the IPG 100. As noted earlier, the pairing data and authentication data exchanged during the pairing process may differ depending on the communication standard used (e.g., Bluetooth).

Once the IPG 100 and RC 50' are paired and connected at time t21, the mode logic 102 in the IPG's control circuitry 38 can exit the pairing mode. However, the IPG 100 is still in the MRI mode. Again, it is preferred for safety that this mode be affirmatively exited by the patient or clinician. Thus, and similarly to what was described earlier (t18, FIG. 5), the user at time t22 can use the GUI of RC 50' to exit the MRI mode. This causes RC 50' to transmit an exit MRI mode instruction to the IPG 100, which is received at the IPG's antenna 34a or 34b. At this point, mode logic 102 can cause the IPG 100 to enter the normal mode, which can automatically cause normal stimulation to begin (and cause any MRI-condition stimulation to stop).

At this point the IPG 100 is paired to RC 50', which probably does not belong to the patient. If and when the patient relocates his RC 50, the IPG 100 can once again be paired to RC 50 using the normal pairing procedure described earlier (FIG. 4). As noted earlier, this can be facilitated because the RC50 and IPG 100 would have stored information about the other (see FIG. 3, memories 106, 110).

FIG. 7 summarize how the mode logic 102 operates upon detecting, or ceasing detecting, a magnetic field in the different circumstances summarized earlier, and also describes the actions that the mode logic 102 can take, which depends upon the current mode in which the IPG is operating. When in the normal mode, if a magnetic field is sensed on for 2 (A) second or more (and then the field is sensed off), it is assumed that the sensed field is coming from bar magnet 90 (FIG. 4). The IPG 100 is reset (t2, FIG. 4), and then preferably automatically enters the pairing mode (t3, FIG. 4), thus allowing the IPG 100 to be paired or reconnected to the patient's RC 50 or any other relevant external device (such as RC 50').

When operating in the MRI mode, the actions taken depend on how long the magnetic field is sensed. If a magnetic field is sensed for 25 (B) second or more, it is assumed that the sensed field is coming from magnet 112 in the MRI machine 100 (FIG. 5). The IPG 100 assumes that an MRI scan will begin shortly, and will start executing MRI protective measures, and will also disable telemetry (t13, FIG. 5). Afterwards, when the magnetic field is not sensed for 30 seconds (C), it is assumed that the MRI magnet 112 has been removed and is no longer proximate to the IPG. At this point, MRI protective measures can be stopped, and telemetry enabled (t17, FIG. 5).

By contrast, if a magnetic field is sensed for a shorter time between 4 (D) and 10 (E) seconds when in the MRI mode, it is assumed that the sensed field is coming from bar magnet 90, and that the pairing mode should commence (t20, FIG. 6). Note that, preferably, D and E are greater than A, and D and E are less than B and/or C.

While the disclosed techniques are discussed in the context of an MRI machine, and the use of an MRI mode to protect the IPG from the MRI machine's magnetic fields, it should be understood that the disclosed techniques can be used more generally to protect the IPG from fields produced by other pieces of equipment, or other medical diagnostic or treatment equipment (collectively, "medical equipment"). In this sense, the MRI mode can be understood more generally as a protective mode.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for controlling an implantable medical device (IMD), comprising:
    using stimulation circuitry in the IMD to provide therapeutic stimulation to a patient at one or more electrodes of the IMD;
    wirelessly receiving at the IMD a first instruction, causing the IMD to enter a protective mode, wherein in the protective mode the IMD is enabled to execute one or more protective measures to protect the IMD from a first field produced by equipment;
    while in the protective mode, wirelessly receiving at the IMD a second instruction instruction, causing the IMD to enter a pairing mode, wherein the pairing mode enables the IMD to pair for communications with a first external device;
    while in the protective mode and the pairing mode, wirelessly receiving at the IMD, from the first external device, a third instruction, causing the IMD and the first external device to pair for communications; and
    while in the protective mode, wirelessly receiving at the IMD, from the first external device, a fourth instruction, causing the IMD to exit the protective mode and to continue providing the therapeutic stimulation.

2. The method of claim 1, wherein the first instruction is wirelessly received at the IMD from a second external device paired for communications with the IMD, wherein the second external device is different from the first external device.

3. The method of claim 1, wherein the second instruction comprises a second field comprising a first magnetic field.

4. The method of claim 3, wherein the first magnetic field is produced by an external magnet.

5. The method of claim 3, wherein the first magnetic field comprises a DC magnetic field.

6. The method of claim 3, wherein the first magnetic field is effective to cause the IMD to enter the pairing mode when the first magnetic field is wirelessly received at the IMD for a first duration.

7. The method of claim 6, wherein the first duration is between a minimum duration and a maximum duration.

8. The method of claim 7, wherein the minimum duration and the maximum duration are stored in the IMD.

9. The method of claim 1, wherein the first field comprises an AC magnetic field produced by the equipment.

10. The method of claim 1, further comprising, while in the protective mode, wirelessly receiving at the IMD a fifth instruction from the equipment, causing the IMD to execute the one or more protective measures.

11. The method of claim 10, wherein the fifth instruction comprises a third field comprising a second magnetic field.

12. The method of claim 11, wherein the second magnetic field is produced by the equipment.

13. The method of claim 12, wherein the second magnetic field comprises a DC magnetic field produced by a magnet in the equipment.

14. The method of claim 11, wherein the second magnetic field is effective to cause the IMD to execute the one or more protective measures when the second magnetic field is wirelessly received at the IMD for a second duration.

15. The method of claim 14, wherein the second magnetic field is effective to cause the IMD to stop executing the one or more protective measures when the second magnetic field is not wirelessly received at the IMD for a third duration.

16. The method of claim 1, further comprising periodically broadcasting pairing data from the IMD when the IMB is in the pairing mode.

17. The method of claim 1, wherein the protective mode comprises a Magnetic Resonance Imaging (MM) mode, and wherein the equipment comprises an MM machine.

18. The method of claim 1, wherein the one or more protective measures comprise one or more of: disabling the stimulation circuitry; providing condition stimulation to the patient different from the therapeutic stimulation; increasing one or more voltages in the IMD; increasing a power supply voltage for the stimulation circuitry; or opening passive charge recovery switches in the stimulation circuitry.

19. An implantable medical device (IMD), comprising:
    a plurality of electrodes;
    stimulation circuitry configured to provide therapeutic stimulation to a patient at one or more of the electrodes; and
    control circuitry configured to:
      receive a first instruction, causing the IMB to enter a protective mode, wherein in the protective mode the IMB is enabled to execute one or more protective measures to protect the IMD from a first field produced by equipment;
      while in the protective mode, receive a second instruction, causing the IMB to enter a pairing mode, wherein the pairing mode enables the IMD to pair for communications with a first external device;
      while in the protective mode and the pairing mode, receive, from the first external device, a third instruction, causing the IMD and the first external device to pair for communications; and
      while in the protective mode, receive, from the first external device, a fourth instruction, causing the IMD to exit the protective mode and to continue providing the therapeutic stimulation.

20. The IMD of claim 19, wherein the one or more protective measures comprise one or more of: disabling the stimulation circuitry; providing condition stimulation to the patient different from the therapeutic stimulation; increasing one or more voltages in the IMD; increasing a power supply voltage for the stimulation circuitry; or opening passive charge recovery switches in the stimulation circuitry.

* * * * *